(12) United States Patent
Zhang et al.

(10) Patent No.: US 10,548,535 B2
(45) Date of Patent: Feb. 4, 2020

(54) METHOD AND APPARATUS FOR MULTI-STATE HEART FAILURE DECOMPENSATION DETECTION

(71) Applicant: Cardiac Pacemakers, Inc., St. Paul, MN (US)

(72) Inventors: Yi Zhang, Plymouth, MN (US); Pramodsingh Hirasingh Thakur, Woodbury, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 843 days.

(21) Appl. No.: 14/178,624

(22) Filed: Feb. 12, 2014

(65) Prior Publication Data
US 2014/0236026 A1   Aug. 21, 2014

Related U.S. Application Data

(60) Provisional application No. 61/766,313, filed on Feb. 19, 2013.

(51) Int. Cl.
*A61B 5/00*        (2006.01)
(52) U.S. Cl.
CPC .................... *A61B 5/7275* (2013.01)
(58) Field of Classification Search
CPC ................ A61B 5/7275; A61B 5/0205
See application file for complete search history.

(56) References Cited

U.S. PATENT DOCUMENTS

| | | | |
|---|---|---|---|
| 6,512,949 B1 | 1/2003 | Combs et al. | |
| 6,575,912 B1 * | 6/2003 | Turcott | A61B 5/02427 600/480 |
| 7,164,947 B2 | 1/2007 | Holmstrom et al. | |
| 7,761,158 B2 | 7/2010 | Brockway et al. | |
| 7,946,995 B1 * | 5/2011 | Koh | A61B 5/0205 600/485 |
| 7,963,922 B2 | 6/2011 | Taepke, II et al. | |
| 7,986,994 B2 | 7/2011 | Stadler et al. | |
| 8,055,335 B2 | 11/2011 | Stylos | |
| 8,219,198 B2 | 7/2012 | Gollasch | |

(Continued)

OTHER PUBLICATIONS

Conraads, V. M, et al., "Sensitivity and positive predictive value of implantable intrathoracic impedance monitoring as a predictor of heart failure hospitalizations: the SENSE-HF trial", Eur Heart J., 32(18), (Sep. 2011), 2266-73.

(Continued)

*Primary Examiner* — Tiffany Weston
(74) *Attorney, Agent, or Firm* — Schwegman Lundberg & Woessner, P.A.

(57) ABSTRACT

Devices and methods for detecting events indicative of heart failure (HF) decompensation status are described. An ambulatory medical device can determine the present physiologic state as being either a drift state or a stable state, and applies an algorithm to detect HF decompensation event according to the physiologic state. In some embodiments, the ambulatory medical device uses the present physiologic state to estimate one ore more expected future signal characteristics, and to detect HF decompensation event using the one or more expected futures signal characteristics.

20 Claims, 9 Drawing Sheets

(56) References Cited

U.S. PATENT DOCUMENTS

| | | | |
|---|---|---|---|
| 8,295,918 B2* | 10/2012 | Rosenberg | A61N 1/3627 |
| | | | 600/509 |
| 2008/0024293 A1 | 1/2008 | Stylos | |
| 2010/0030292 A1 | 2/2010 | Sarkar et al. | |
| 2010/0298904 A1 | 11/2010 | Blomqvist et al. | |
| 2011/0172545 A1* | 7/2011 | Grudic | A61B 5/021 |
| | | | 600/485 |
| 2011/0251496 A1 | 10/2011 | Taepke, II et al. | |
| 2011/0301491 A1 | 12/2011 | Stadler et al. | |

OTHER PUBLICATIONS

Sarkar, S., et al., "Improved algorithm to detect fluid accumulation via intrathoracic impedance monitoring in heart failure patients with implantable devices.", J Card Fail., 17(7), (Jul. 2011), 569-76.

* cited by examiner

METHOD AND APPARATUS FOR MULTI-STATE HEART FAILURE DECOMPENSATION DETECTION

CLAIM OF PRIORITY

This application claims the benefit of priority under 35 U.S.C. § 119(e) of U.S. Provisional Patent Application Ser. No. 61/766,313, filed on Feb. 19, 2013, which is herein incorporated by reference in its entirety.

TECHNICAL FIELD

This document relates generally to medical devices, and more particularly, to systems, devices and methods for detecting and monitoring heart failure decompensation.

BACKGROUND

Congestive heart failure (CHF) is a major health problem and affects over five million people in the United States alone. CHF patients typically have enlarged heart with weakened cardiac muscles, resulting in poor cardiac output of blood. Elevated pulmonary vascular pressures can cause fluid accumulation in the lungs over time. In many CHF patients, fluid accumulation precedes episodes of heart failure (HF) decompensation.

SUMMARY

Frequent monitoring of CHF patients and timely detection of intrathoracic fluid accumulation or other events indicative of HF decompensation status can help prevent worsening of HF in CHF patients, hence reducing cost associated with HF hospitalization.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory or implantable medical devices can be configured to sense electrical activity and mechanical function of the heart, and to optionally deliver therapy such as electrical stimulation pulses to a target area, such as to restore or improve the cardiac function. Some of these devices can include one or more diagnostic features, such as using transthoracic impedance. For example, fluid accumulation in the lungs decreases the transthoracic impedance due to the lower resistivity of the fluid than air in the lungs.

Desirable performance of a method or a device of detecting HF decompensation can include one or more of a high sensitivity, a high specificity, or a high positive predictive value (PPV). In the context of HF decompensation event detection, the sensitivity can represent a percentage of actual HF decompensation episodes that are correctly recognized by a detection method; the specificity can represent a percentage of actual non-HF decompensation episodes that are correctly recognized as non-HF decompensation events by the detection method; and the PPV can represent a percentage of the detected HF decompensation episodes, as declared by the detection method, that are actual HF decompensation events. A high sensitivity can help ensure timely intervention to a patient with an impending HF decompensation episode, whereas a high specificity and a high PPV can help avoid unnecessary intervention and added healthcare cost due to false alarms. A number of factors may affect the performance of a detector, such as implantable device pocket and lead maturation following the device implantation. Therefore, the present inventors have recognized that there remains a considerable need of devices and methods that can detect HF decompensation events with reduced false positive detections in CHF patients.

Various embodiments described herein can help improve the process of detecting events indicative of HF decompensation status. For example, an ambulatory medical device (such as an implantable medical device or a wearable medical device) can detect an HF decompensation event, such as using physiologic state information. A signal sensing circuit can be configured to sense a physiologic signal indicative of the patient's heart failure decompensation status. A physiologic state analyzer circuit can include a timer or a clock configured to determine a current elapsed time since a physiologic state trigger event. The physiologic state analyzer circuit can also include a drift metric calculator circuit configured to calculate a drift metric. The physiologic state analyzer circuit may be configured to determine a physiologic state of the patient such as using at least one of the elapsed time or the calculated drift metric, and the HF decompensation event detector circuit may be configured to detect an indication of HF decompensation status using the determined physiologic state and the sensed physiologic signal.

A method can include detecting an indication of HF decompensation status in a patient having an ambulatory medical device. The method can include sensing a physiologic signal indicative of the HF decompensation status, determining a physiologic state of the patient using at least one of a time from a physiologic state trigger event and a drift metric of the physiologic signal, and detecting the indication of HF decompensation status using the determined physiologic state and the sensed physiologic signal. The drift metric may be computed by comparing first measurements of the physiological signal obtained during a first time window and second measurements of the physiologic signal obtained during a non-overlapping second time window. The drift metric may also be computed using a function of a first or higher order derivative of the physiological signal obtained from two or more non-identical time windows.

A method for detecting HF decompensation events can include sensing a physiologic signal indicative of the HF decompensation status, calculating at least one expected future signal characteristic using the sensed physiologic signal, comparing the at least one expected future signal characteristic to at least one criterion, and using the comparison for determining the indication of HF decompensation status.

This Summary is an overview of some of the teachings of the present application and not intended to be an exclusive or exhaustive treatment of the present subject matter. Further details about the present subject matter are found in the detailed description and appended claims. Other aspects of the present application will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodi

DETAILED DESCRIPTION

Disclosed herein are systems, devices, and methods for detecting one or more events indicative of HF decompensation status. The events can include early precursors of an HF decompensation episode. That is, these events can occur well before the systematic manifestation of worsening of HF. Therefore, by detecting the precursor events, the present document can provide a method and device to predict the impending HF decompensation episode. In particular, the methods and devices described herein can be applicable to detecting accumulation of intrathoracic fluid that can forecast an impending HF decompensation episode. More generally, the systems, devices, and methods described herein may be used to determine HF status and/or track HF progression such as worsening and recovery from an event.

Figure 1:
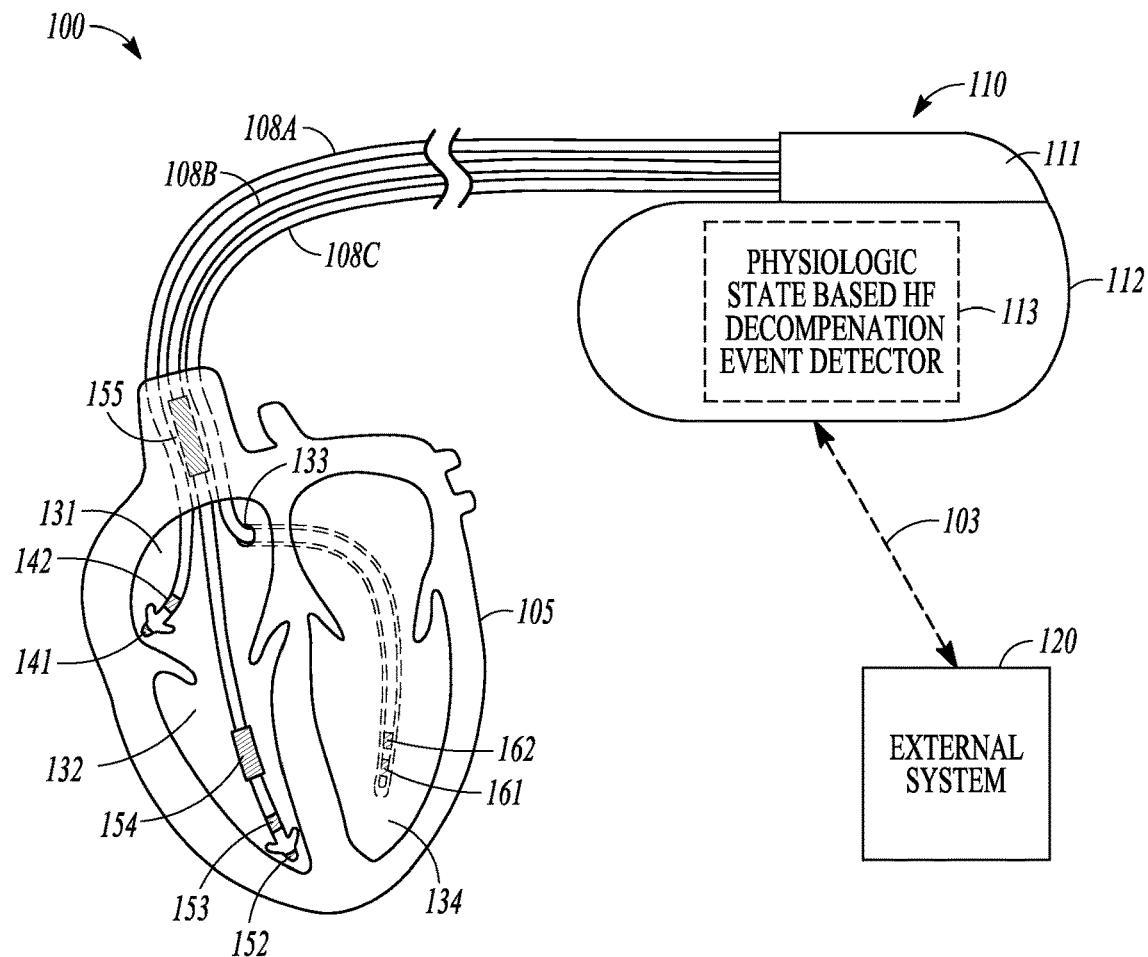
- FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

As illustrated, the CRM system 100 can include a physiologic state based HF decompensation event detector 113. The physiologic state based HF decompensation event detector 113 can include a physiologic state analyzer that can detect the present physiologic state as being one of a plurality of pre-defined states, and an HF decompensation event detector that can detect from a physiological signal an event indicative of HF decompensation status using physiologic state information. The physiologic state analyzer can detect a present physiologic state, such as using a first signal that can be acquired from electrodes on one or more of the leads 108A-C. The HF decompensation event detector can detect an HF decompensation event, such as from a second signal that can be acquired from electrodes on one or more of the leads 108A-C. The HF decompensation event can include one or more early precursors of an HF decompensation episode, or an event indicative of HF progression such as recovery or worsening of HF status. The first signal used by the physiologic state analyzer and the second signal used for HF decompensation event detection can be obtained from the same physiological signal. Examples of a physiologic state based HF decompensation event detector circuit 113 are described below, such as with reference to FIGS. 2-4.

The external system 120 can allow for programming of the IMD 110 and can receives information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The physiologic state based HF decompensation event detector circuit 113 may be implemented at the external system 120, which can be configured to perform HF decompensation event detection such as using data extracted from the IMD 110 or data stored in a memory within the external system 120. Portions of the physiologic state based HF decompensation event detector circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to IMD 110, CRM system 100 could include a subcutaneous medical device (e.g., subcutaneous ICD, subcutaneous diagnostic device), wearable medical devices (e.g., patch based sensing device), or other external medical devices.

Figure 2:
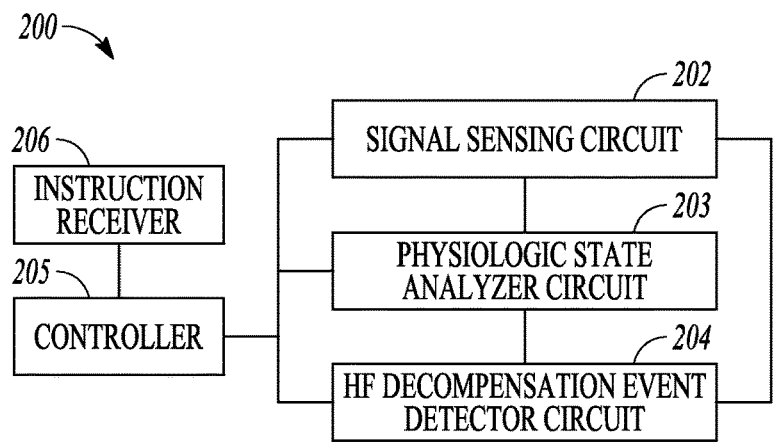
FIG. 2 illustrates an example of a physiologic state based HF decompensation event detector.

FIG. 2 illustrates an example of a physiologic state based HF decompensation event detector 200, which can be an embodiment of the physiologic state based HF decompensation event detector 113. The physiologic state based HF decompensation event detector 200 can include one or more of a signal sensing circuit 202, a physiologic state analyzer circuit 203, an HF decompensation event detector circuit 204, a controller 205, and an instruction receiver 206.

The signal sensing circuit 202 can be configured to sense a physiological signal, such as for HF decompensation event detection. The signal sensing circuit 202 can be coupled to one or more of: one or more electrodes, one or more sensors, or one or more patient monitors, such as electrodes on one or more of the leads 108A-C or the can 112. The sensing circuit 202 can be configured to sense a physiological signal, such as can be indicative of HF decompensation status. Examples of such a physiological signal can include one or more electrograms, such as from electrodes on one or more of the leads 108A-C or the can 112, intrathoracic impedance, intracardiac impedance, arterial pressure, pulmonary artery pressure, RV pressure, LV coronary pressure, coronary blood temperature, blood oxygen saturation, one or more heart sounds, one or more respiration signals such as a respiration rate signal or a tidal volume signal. The signal sensing circuit 202 can include one or more modules to perform signal conditioning (e.g., signal amplification, digitization, or filtering) or parameter extraction from the sensed physiological signal. Examples of extracted signal parameters can include: signal mean, median, or other central tendency measures; a histogram of the signal intensity; one or more signal trends over time; one or more signal morphological descriptors; or signal power spectral density at a specified frequency range. In an example, the signal sensing circuit can sense two or more physiological signals and can generate a composite signal parameter set such as using the two or more physiological signals.

The physiologic state analyzer 203 can be configured to determine the present physiologic state as one of a plurality of pre-determined physiologic states. A physiologic state can represent a patient condition or a device status. The pre-determined physiologic states can include a drift state and a stable state. The physiologic state analyzer 203 can be configured to determine the present physiologic state, such as by analyzing information from the physiological signal received from the signal sensing circuit 202, or from another data storage in the IMD 110 or in the external system 120. The physiologic state analyzer 203 can be configured to determine the present physiologic state such as using one or more modules that can determine the current physiologic state individually or jointly, such as discussed below with reference to FIG. 3.

The HF decompensation event detector circuit 204 can receive input from the signal sensing circuit 202 and the physiologic state analyzer 203 and can be configured to detect the presence of an event indicative of HF decompensation status. The HF decompensation event detector circuit 204 can include a detection parameter updating circuit that can be configured to update one or more parameters used in HF decompensation event detection such as according to the present physiologic state. The decompensation event detector circuit 204 can be configured to select and execute one from a plurality of HF decompensation detection algorithms, such as according to the present physiologic state detected by the physiologic state analyzer 203.

The controller 205 can be configured to control the operation of components 202-204 and the data flow among these components. The controller 205 can receive external programming input from the instruction receiver 206, such as to control one or more of the signal sensing, the physiologic state analysis, or the HF decompensation event detection. The instruction receiver 206 can be coupled to a user interface on the external system 120, which can present one or more programming options and can receives the user's programming input. Examples of the instructions that can be received by instruction receiver 206 can include: selection of the electrodes used for physiological signal sensing, selection of the source of data used for physiologic state analysis, selection of one or more physiologic state analysis algorithms or associated parameter values of the physiologic state analyzer 203, or selection of one or more algorithms or associated parameter values of the HF decompensation event detector 204.

Figure 3:
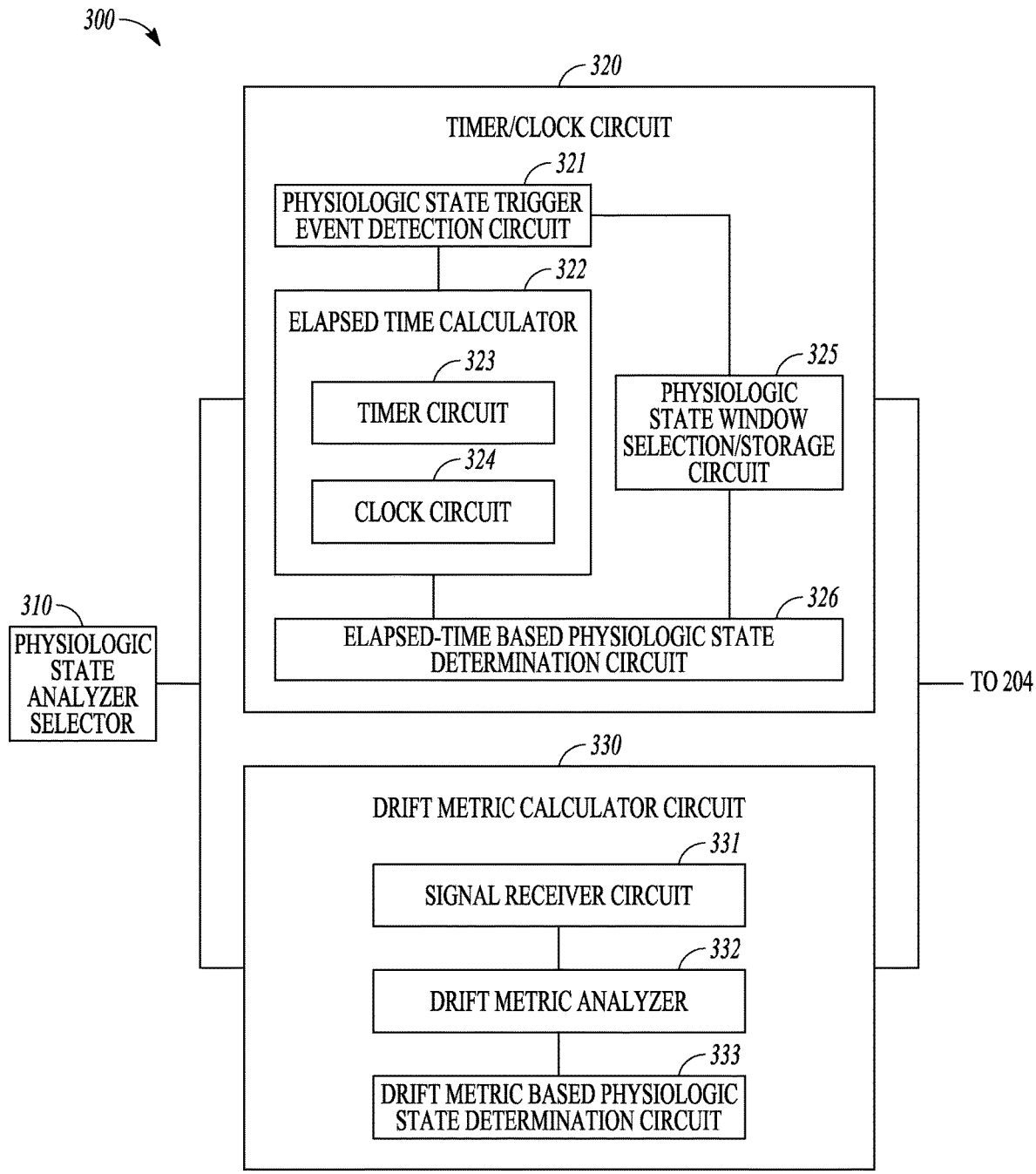
FIG. 3 illustrates an example of a physiologic state analyzer.

FIG. 3 illustrates an example of the physiologic state analyzer 300, which can be an embodiment of physiologic state analyzer 203. The physiologic state analyzer 300 can include one or more of a physiologic state analyzer selector 310, a time/clock circuit 320, or a drift metric calculator circuit 330.

The physiologic state analyzer selector 310 can be configured to receive external programming input and to select one or both of the time/clock circuit 320 or the drift metric calculator circuit 330, such as to decide the present physiologic state. The physiologic state analyzer selector 310 can be configured to receive external programming input such as from the instruction receiver 206.

The time/clock circuit 320 can be configured to determine the present physiologic state such as using the elapsed time since a physiologic state trigger event. The timer/clock circuit 320 can include one or more of a physiologic state trigger event detection circuit 321, an elapsed time calculator 322, a physiologic state window selection/storage circuit 325, or an elapsed-time based physiologic state determination circuit 326.

The physiologic state trigger event detection circuit 321 can be configured to detect a trigger event related to a change in the patient's health or disease status, a change of the functional status of an ambulatory medical device, or a change of the interaction between the patient and the ambulatory medical device. Specifically, the trigger events can include, for example, a placement of an ambulatory medical device, a replacement of the ambulatory medical device, a surgical repositioning of the ambulatory medical device or associated parts, a delivery of therapy from the ambulatory medical device, a cardiac surgery, a discharge of the patient from a hospital, or a development of a medical condition indicative of a change of cardiopulmonary function. In some embodiments, a trigger event can include a combination of more than one conditions (for example, HF hospitalization and device reprogramming), or variation of one or more conditions (for example, a delivery of two consecutive shocks within 24 hours).

The detection of a physiologic state trigger event may be passive or active. In some embodiments, the physiologic state trigger event detection circuit 321 can receive from external user input the occurrence and the type of trigger event. In some embodiments, the physiologic state trigger event detection circuit 321 can receive a physiological signal from the signal sensing circuit 202 or from another signal source in the IMD 110 or the external system 120, and actively detects a trigger event. The detected trigger event can be presented to the user via a user interface on the external system 120, and the system is configured to allow the user to confirm the detected trigger event.

The elapsed time calculator 322 can determine the elapsed time since the occurrence of the physiologic state trigger event. The elapsed time determination circuit 322 can include one or both of a timer circuit 323 and a clock and memory circuit 324. The timer circuit 323 can receive input from the trigger event detection circuit 32 and reset the timer when the trigger event occurs. When the physiologic state analyzer 300 receives a command of determining the present physiologic state, the elapsed time since the physiologic trigger event is determined from the timer circuit. The clock circuit 324 can receive an input from the trigger event detection circuit 321, and stores the time of the trigger event in a memory. When the physiologic state analyzer 300 receives a command of determining the present physiologic state, the elapsed time since the physiologic trigger event is determined from the clock circuit 324 as the difference between the present clock time and the time of the trigger event.

The physiologic state window selection/storage circuit 325 can choose values for a time window ($T_{W1}$, $T_{W2}$), where $T_{W1}$ and $T_{W2}$ represent the beginning and the end time of the time window, respectively, with reference to the physiologic state trigger event. In an example, the physiologic state window selection/storage circuit 325 can be coupled to a user interface on the external system 120 which allows user to interactively program the values for the window, or to choose from a list of pre-stored values in the storage/selection circuit 325. In another example, a plurality of values of $T_{W1}$ and $T_{W2}$ can be indexed by the type of physiologic state trigger event or a configuration for sensing the physiologic signal, and stored in the storage circuit 325 in a format of a look-up table, an association list or map, or other searchable data structures. The physiologic state window selection/storage circuit 325 can receive from the physiologic state trigger event detection circuit 321 an input of the type of trigger event or a configuration for sensing the physiologic signal, and determine the values for $T_{W1}$ and $T_{W2}$ by searching through the pre-stored time window data structures.

The elapsed-time based physiologic state determination circuit 326 can receive the elapsed time from the elapsed time calculator 322 and the time window ($T_{W1}$, $T_{W2}$) from the physiologic state window selection/storage circuit 325, and determines the present physiologic state. In an example, the present physiologic state can be determined using whether the elapsed time is within the time window ($T_{W1}$, $T_{W2}$). Examples of elapsed-time based detection of physiologic state is discussed below, such as with reference to FIG. 6.

The rift metric calculator circuit 330 can include a signal receiver circuit 331, a drift metric analyzer 332, and a drift metric based physiologic state determination circuit 333. In an example, the signal receiver circuit 331 can receive a physiological signal from the signal sensing circuit 202. In another example, the signal receiver circuit 331 can retrieve signal from the IMD 110, the external device 120, or other external data source. Examples of signals received include impedance signals, respiration signals, coronary blood temperature, blood oxygen saturation, or heart sound signal. The signal receiver circuit 331 can receive two or more physiological signals.

The Drift metric analyzer 332 can calculate a drift metric using the signal from signal receiver circuit 331. In an example, the drift metric analyzer 332 can take two data segments from the received physiological signal during non-overlapped time windows W1 and W2, compute a first measurement F1 using data in window W1 and a second measurement F2 using data in window W2, and generate a drift metric using a comparison between the first measurement F1 and the second measurement F2. In another example, the drift metric analyzer 332 can take data segments from the received physiological signal during two or more mutually non-identical time windows, and compute drift metric as a function of one or more first or higher order derivatives of data segments in the time windows.

The drift metric based physiologic state determination circuit 333 receives the calculated drift metric from the drift metric analyzer 332 and determines the present physiologic state. In an example, the drift metric can be compared to a pre-determined drift metric threshold. The physiologic state can be determined using a plurality of estimates of the drift metric computed by drift metric analyzer 332. The drift metric based physiologic state determination circuit 333 determines the physiologic state such as using a count of the estimates of the drift metric that satisfy at least one specified criterion. Examples of drift metric calculation and drift-metric based detection of physiologic state is discussed below, such as with reference to FIGS. 7-9.

Figure 4:
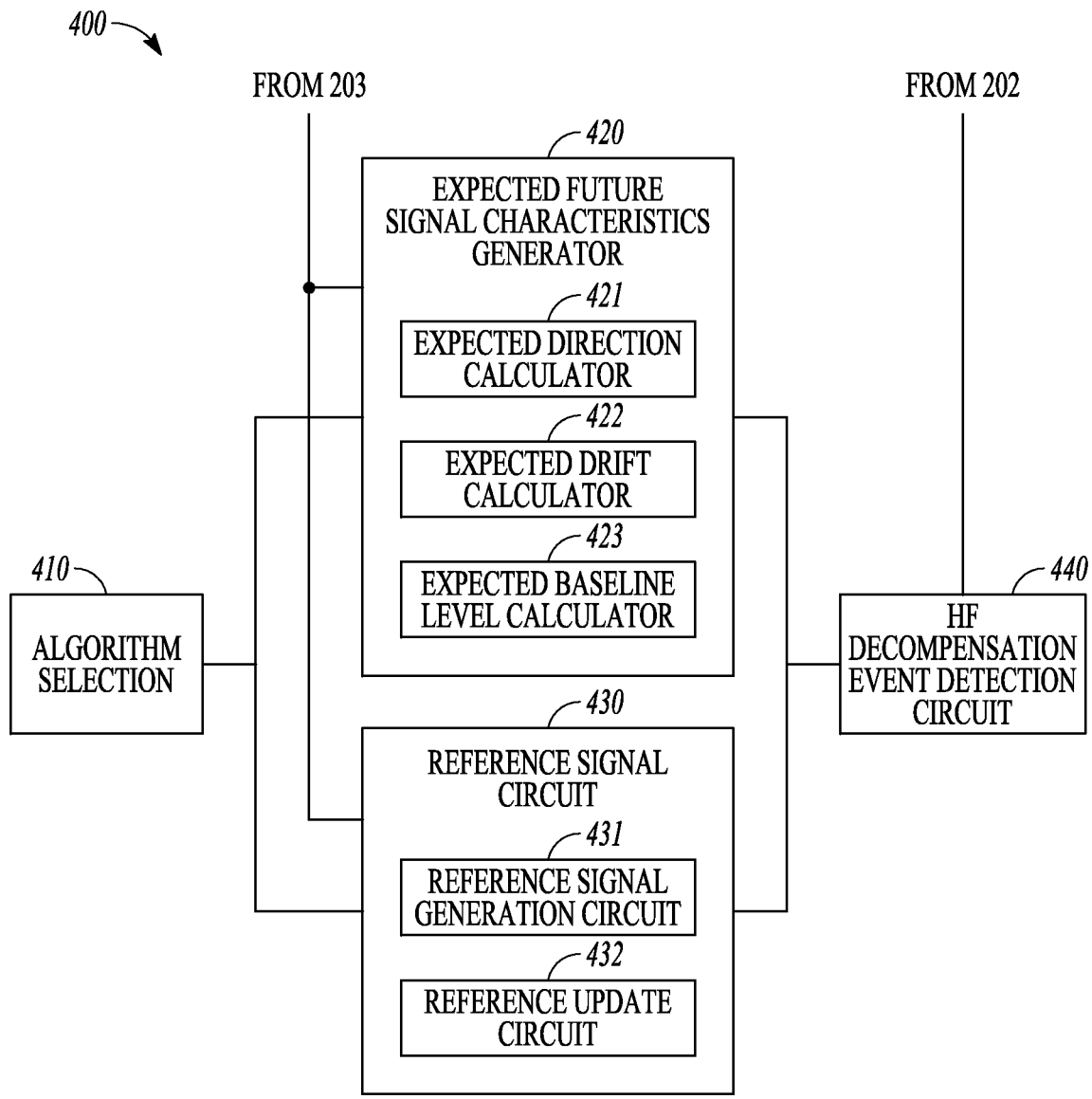
FIG. 4 illustrates an example of an HF decompensation event detector.

FIG. 4 illustrates an example of an HF decompensation event detector 400, which can be an embodiment of HF decompensation event detector 204. The HF decompensation event detector 400 can include an algorithm selection circuit 410, an expected future signal characteristics generator 420, a reference signal circuit 430, and an HF decompensation event detection circuit 440.

The algorithm selection circuit 410 can receive an external input to select one or both of the expected future signal characteristics generator 420 and reference signal updating circuit 430 for detecting an HF decompensation event. In an example, the algorithm selection circuit 410 can receive external programming input from the instruction receiver 206.

The expected future signal characteristics generator 420 can include one or more future signal characteristics calculation circuits, including an expected direction calculator 421, an expected drift calculator 422, or an expected baseline level calculator 423. Each future signal characteristic calculation circuit can calculate an expected future signal characteristic such as using the historical data from the physiological signal provided by the signal sensing circuit 201. The expected direction calculator 421 can determine a trend of the physiological signal intensity as being one of upward direction, downward direction, or remaining flat. The expected drift calculator 422 can calculate one or more of a drift from the physiological signal, a quantity of change or rate of change of physiological signal intensity. The expected baseline level calculator 423 can calculate an expected baseline such as using the historical data from the physiological signal. In addition to the future signals characteristics as illustrated in FIG. 4, the present inventors also contemplated other signal characteristics, such as signal intensity or morphological characteristics calculated in time, frequency, or joint time-frequency domain.

In an example, as illustrated in FIG. 4, the expected future signal characteristics generator 420 can receive an input from the physiologic state analyzer 203. One or more characteristics calculators may be activated or deactivated according to the present physiologic state. For example, expected baseline level calculator 423 is activated only if the present physiological state is stable state. In another example, the parameters used by the characteristics calculators can vary according to the physiologic state. Examples of expected future signal characteristics calculation is discussed below, such as with reference to FIG. 11.

The reference signal circuit 430 can include a reference signal generation circuit 431 and a reference update circuit 432. A reference signal may represent a trend of the signal intensity in history. In an example, the reference signal generation circuit 431 can generate a reference signal by filtering the physiological signal in time or frequency domain. Examples of filtering methods can include: a moving average filter, autoregressive model filter, autoregressive and moving average filter; low-pass, high-pass, or band-pass filters; linear or nonlinear filters; or static or adaptive filters. In some examples, filtering of the physiological signal can be operated on a specified time period. In another example, the reference signal generation circuit 431 can generate the reference signal after a specified period of time following a physiologic event such as a device implant.

The reference update circuit 432 can update the reference signal when a specified criterion is met. In an example, the reference update circuit 432 can receive an input from the physiologic state analyzer 203 and update the reference signal only if the present physiologic state is drift state. The reference signal can be updated by adding a reference correction factor calculated from the physiological signal. In an example, the reference correction factor can be computed as the drift metric. For example, the physiological signal can be processed by the drift metric analyzer 332, and the reference correction factor can be determined as the difference between the average intensity of the physiological signal segments in two non-overlapping windows.

The HF decompensation event detection circuit 440 can receive the physiological signal from the signal sensing circuit 202 and detect an HF decompensation event from the physiological signal. In an example, the HF decompensation event detection circuit 440 can generate a decompensation index such as using the physiological signal and the reference signal generated by reference signal circuit 430. The decompensation index can be a quantitative parameter indicating the presence or severity of a physiologic condition precipitating an HF decompensation episode, such as excessive intrathoracic fluid accumulation. In an example, an HF decompensation event is detected if the decompensation index is greater than a threshold. In another example, the HF decompensation event detection circuit 440 can detect the HF decompensation event such as using a comparison between an expected future signal characteristics provided by the expected future signal characteristics generator 420 and the signal characteristics provided by the signal sensing circuit 202. An HF decompensation event is deemed detected if at least one of the measured signal characteristics significantly deviates from the corresponding predicted signal characteristics. Examples of HF decompensation event detection is discussed below, such as with reference to FIGS. 10-11.

Figure 5:
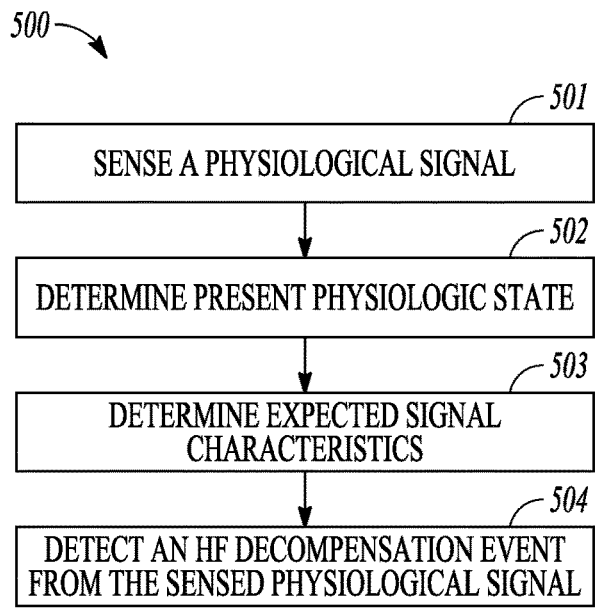
FIG. 5 illustrates an example of a method for detecting an event indicative of HF decompensation status such as using physiologic state information.

FIG. 5 illustrates an example of a method 500 for detecting an event indicative of HF decompensation status such as using present physiologic state information. The event can include one or more early precursors of an HF decompensation episode, or an event indicative of HF progression such as recovery or worsening of HF status. In some embodiments, the method can be applied to operate the IMD 110 or the external system 120 in communication with the IMD 110. The method can be performed by the physiologic state based HF decompensation event detector 113.

At 501, a physiological signal is sensed. Examples of the physiological signal can include electrograms from electrodes on leads 108A-C and the can 112, intrathoracic impedance, intracardiac impedance, arterial pressure, pulmonary artery pressure, RV pressure, LV coronary pressure, coronary blood temperature, blood oxygen saturation, heart sounds, or respiration signals which can include respiration rate signal or tidal volume signal. The physiological signals can be sensed by one or more electrodes or one or more external sensors attached to or implanted in a patient. At 502, the physiological signal can be analyzed and the current physiologic state can be determined as one of a plurality of pre-determined physiologic states. A physiologic state may represent a health or disease state of the patient, or a device state in response to the patient's disease progression. Examples of the physiologic state can include an acute state post device implant, chronic state post device implant, drift state where the physiological signal indicates a change not in conformity of the change in HF decompensation status, or a stable state where the physiological signal indicates a change in conformity of the change of HF decompensation status.

As illustrated in FIG. 5, the physiological signal sensed at 501 can be used for determining current physiologic state or for HF decompensation event detection. In some embodiments, the signal used for determining the present physiologic state at 502 can be different than the physiologic signal at 501. For example, a heart sound signal acquired by an implantable accelerometer is used for determining the present physiologic state, while an intrathoracic impedance sensor is used to detect an indication of HF decompensation status. In yet another embodiment, the physiological signal at 501 and the signal used for determining the physiologic state at 502 can be different physiological signals extracted from a common physiological sensor. For example, a tidal volume (of respiration) signal can be derived from an intrathoracic impedance sensor and used for determining the present physiologic state at 502, while the intrathoracic impedance signal sensed by the same sensor can be used for detecting an HF decompensation event.

At 503, one or more expected signal characteristics can be determined such as by using the present physiologic state. The expected signal characteristics can include projections of the signal trend such as using the historical physiological data from the same patient. In an example, if the physiologic state is a drift state, the expected characteristic determined for that state can include an expected signal direction indicating the trend of physiological signal intensity, or an expected drift which can be a quantitative measure of change or rate of change of signal intensity. If the physiologic state is a stable state, the expected characteristic determined for that state can include an expected signal direction, or an expected stable baseline. In another example, the expected signal characteristic can include a reference signal, which can be computed also using the historical physiological data from the patient. The expected signal can be updated according to the current physiologic state. In another example, the reference signal can be updated if the current physiologic state is a drift state. The reference signal remains unchanged if the current physiologic state is a stable state.

The sensed physiological data is compared to the determined expected signal characteristic at 504, and an HF decompensation event can be declared if the comparison between the sensed physiological signal and the expected signal characteristic meets a specified criterion. In an example, an HF decompensation event is declared if the difference between the sensed physiological signal and the expected signal characteristic is greater than a pre-determined threshold value. In another example, the comparison between the sensed physiological and the expected signal characteristics can be used to update a metric representing the accumulative variation of the sensed physiological signal around the expected signal characteristics.

Figure 6:
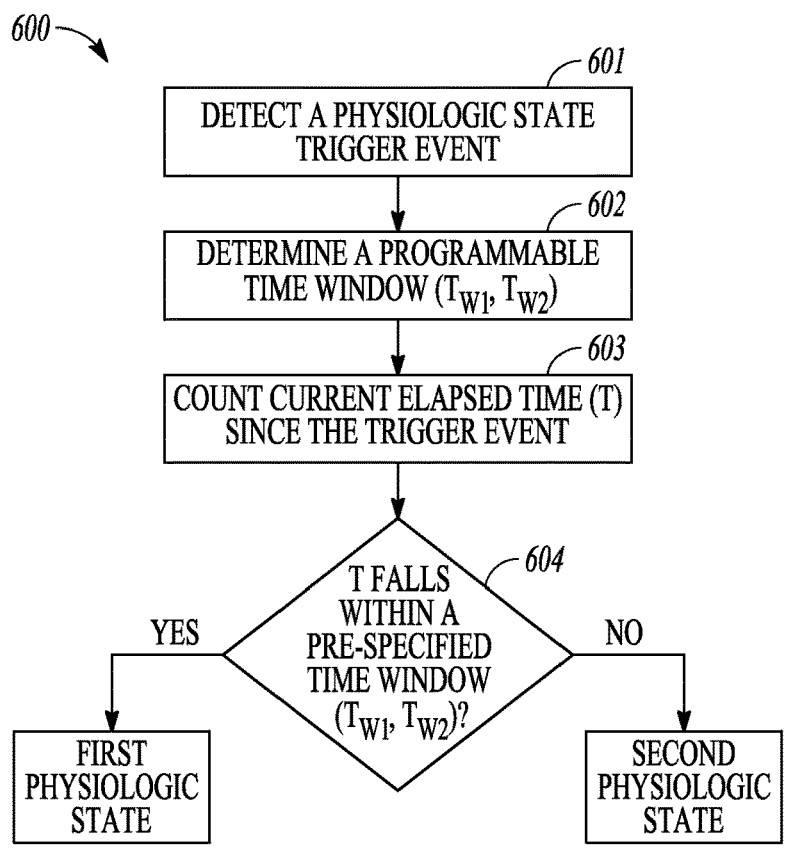
FIG. 6 illustrates an example of a method for determining a current physiologic state such as using time elapsed from a physiologic state trigger event.

FIG. 6 illustrates an example of a method 600 for determining present physiologic state such as using elapsed time from a physiologic state trigger event. The method 600 is a specific embodiment of 502. In some embodiments, the method 600 can be performed by the timer/clock circuit 320.

The process starts with detection of a physiologic state trigger event at 601. The physiologic state trigger event can be an event related to a change in the patient's health or disease status, a change of the status of the implantable medical devices, or a change in the interaction between the patient and the implantable devices. Examples of such physiologic trigger events can include a placement of an ambulatory medical device, a replacement of the ambulatory medical device, a surgical repositioning of the ambulatory medical device or associated parts, a delivery of therapy from the ambulatory medical device, a cardiac surgery, a discharge of the patient from a hospital, or a development of a medical condition indicative of a change of cardiopulmonary function. In some examples, the physiologic state trigger event can be a combination of two or more conditions (e.g., HF hospitalization and device reprogramming), or a variation of one or more of these conditions (e.g., a delivery of two consecutive shocks within 24 hours). In an example, the physiologic state trigger event can be detected from an external user input about the occurrence and the type of trigger event. In another example, the physiologic state trigger event can be automatically detected such as using a physiological signal.

At 602 a programmable time window ($T_{W1}$, $T_{W2}$) is determined. $T_{W1}$ and $T_{W2}$ denote the beginning and the end of the window referenced to the physiologic state trigger event, respectively. The window ($T_{W1}$, $T_{W2}$) describes a period following the physiologic state trigger event during which the physiologic state is likely to be in a known state. The time window may also be defined in other equivalent forms such as using the beginning of the window ($T_{W1}$) and the duration of the window ($t_W$), and the end of the window $T_{W2}$ can be computed as $T_{W2}=T_{W1}+t_W$.

The programmable time window ($T_{W1}$, $T_{W2}$) can be determined using population data. For example, the programmable time window for a post IMD implant event can be chosen to be (0, 6 months) based in part on the analysis of post-implant intrathoracic impedance signal trend data from patient population who demonstrate a drift in intrathoracic impedance during this period. In another example, ($T_{W1}$, $T_{W2}$) can be chosen according to the type of trigger event. For example, ($T_{W1}$, $T_{W2}$) can be programmed to (0, 100 days) for a new IMD implant event, (0, 5 days) for a revision of implantable lead, or (0, 30 days) for an event of patient discharge from the hospital.

The programmable time window ($T_{W1}$, $T_{W2}$) can also be chosen according to the sensing configuration of the physiological signal. For example, in detecting an HF decompensation event using one or more impedance signals, different time window ($T_{W1}$, $T_{W2}$) can be chosen according to the configuration of the impedance vector. For example, ($T_{W1}$, $T_{W2}$) can be programmed to (0, 50 days) if the impedance is sensed using electrodes on an RV lead ($Z_{RV}$), (0, 60-100 days) if the impedance is sensed using electrodes on an RA lead ($Z_{RA}$), or (0, 50 days) if the impedance is sensed using electrodes on a defibrillation lead ($Z_{Shock}$). In another example, the programmable window ($T_{W1}$, $T_{W2}$) can be determined using the historical data from the patient under the similar condition, such as the similar trigger event or similar configurations under which the physiological signal is acquired.

In an example, a searchable data structure such as a lookup table or association map can be created and stored to facilitate automatic selection of time window. The data structure contains a plurality of values of $T_{W1}$ and $T_{W2}$ indexed by one or both of the type of physiologic state trigger event and the configuration for sensing the physiologic signal. Then at 602, ($T_{W1}$, $T_{W2}$) can be determined using the physiologic state trigger event information obtained at 601.

At 603, when a command of determining the physiologic state is issued, the elapsed time (T) from the trigger event can be determined either by computing the difference between the current time and time of the trigger event or by retrieving the time counts from a timer. The timer can be reset at the occurrence of the physiologic state trigger event. The elapsed time can be in the unit of minutes, hours, days, weeks, months or other time units. Then, at 604, the elapsed time is compared to the programmed window ($T_{W1}$, $T_{W2}$). In an example with two pre-determined physiologic states, as illustrated in FIG. 6, the physiologic state is declared to be a first state if T falls within the window ($T_{W1}$, $T_{W2}$), i.e., $T_{W1} \leq T \leq T_{W2}$, or the physiologic state is declared to be a second state if T falls outside the window ($T_{W1}$, $T_{W2}$), i.e., $T<T_{W1}$ or $T>T_{W2}$. In another example where more than two physiologic states are considered, more than one window can be determined, and a particular physiologic state is declared if T falls within a specified region defined by the time windows.

Figure 7:
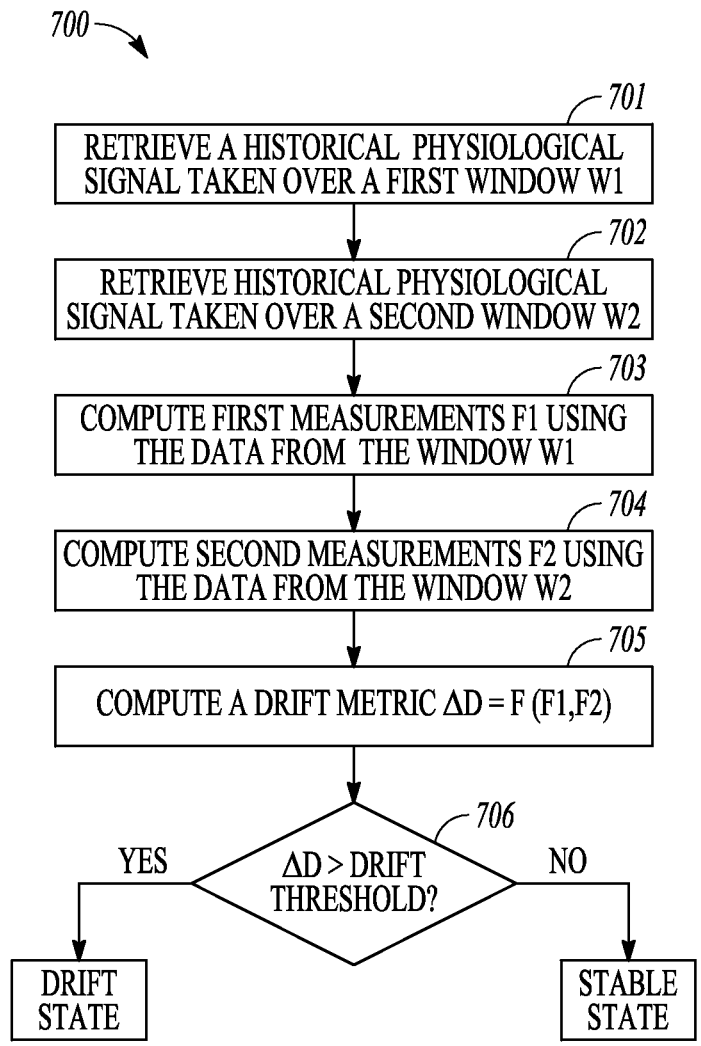
FIG. 7 illustrates an example of a method for determining a current physiologic state such as using a drift metric computed from segments of a physiological signal.

FIG. 7 illustrates an example of a method 700 for determining a present physiologic state such as using a drift metric computed from segments of a physiological signal. The method 700 is an embodiment of 502. In some embodiments, the method 700 can be performed by the drift metric calculator circuit 330.

At 701, a first segment of physiological data can be taken from the patient's historical physiological signal during a time window W1. One or more of the beginning, end, or the size of the time window W1 can be made programmable. In an example, the historical physiological signal can be the physiological signal sensed at 501. In another example, the historical physiological signal can be stored in the IMD 110 or an external system 120. Examples of the historical physiological signal can include one or more impedance signal, respiration signal, coronary blood temperature, blood oxygen saturation, or heart sound signal. In some embodiments, more than one physiological signal is used to determine the physiologic state. Similarly, at 702, a second segment of data can be taken from the same physiological signal during a second time window W2. One or more of beginning, end, or size of W2 may be programmed independently from the programming of W1. In an example, W2 can be programmed such that it does not overlap with the first window W1. That is, W1 and W2 can share no common data point. In another example, W2 can be non-identical to W1. That is, W1 and W2 can differ by at least one data point. This may be achieved by programming at least one of the beginning, end, or size of W2 to a different value than the corresponding parameter for W1.

At 703, first measurements F1 can be computed using the physiological data in W1. Examples of the measurements can include: mean or average, median, mode or any other measures of central tendency; range, quartile range, percentile range, standard deviation, variance, coefficient of variance, and other measurement of dispersion; skewness or histograms; moving average or other means of data trend; or linear or nonlinear regression or other fitted curve with minimal fitting error. In yet another embodiment, the physiological data can include the intensity or the timing information, and the measurement F1 can be a centroid or another measurement indicative of the "center of gravity" of the data in the window. The centroid or center of gravity contains both the intensity and the timing information.

Similarly, at 704, second measurements F2 can be computed using the physiological data in W2. In an example, F1 and F2 can be computed using the same method. For example, F2 can be computed using the same central-tendency measure as that used for calculating F1, but is applied to data in a non-overlapping window W2. In another example, F2 can be computed such as using the same centroid method as that used for calculating F1, but is applied over data in a non-identical window W2.

At 705, a drift metric can be computed as a function of the first measurements F1 and the second measurements F2. In an example, the drift metric can be the difference between F1 and F2. In another example, the drift metric can be a ratio between F1 and F2. In yet another embodiment, both F1 and F2 can be centroids of data within their respective windows, i.e., F1=(t1, X1) and F2=(t2, X2), where t denotes the time and X denotes the intensity of the centroid. The drift metric $\Delta D$ can be determined as the slope of a straight line connecting F1 and F2, i.e., $\Delta D=(X2-X1)/(t2-t1)$. The drift metric thus calculated can represent an estimate of the rate of change of the physiological signal intensity.

The drift metric calculation may not be limited to two windows as illustrated in FIG. 7. In an example, three or more windows of data from the historical physiological signal can be created, and the drift metric can be calculated as a function of the measurements from each window. In a specific example, the physiological data segments can be retrieved during three time windows W1, W2 and W3. F1, F2, and F3 are centroids of window W1, W2, and W3, respectively. That is, F1=(t1, X1), F2=(t2, X2), and F3=(t3, X3). The drift metric $\Delta D$ is an estimate of the "acceleration" of the physiological signal intensity, which can be computed as the second-order derivative: $\Delta D=(S2-S1)/((t3-t1)/2)$, where S1 is the slope of the straight line connecting F1 and F2, i.e., $S1=(X2-X1)/(t2-t1)$, and S2 is the slope of the straight line connecting F2 and F3, i.e., $S2=(X3-X2)/(t3-t2)$.

At 706, the drift metric can be compared to a drift metric threshold. If the drift metric is greater than the drift threshold, then the physiologic state is deemed a drift state; otherwise, the physiologic state is deemed a stable state.

Figure 8:
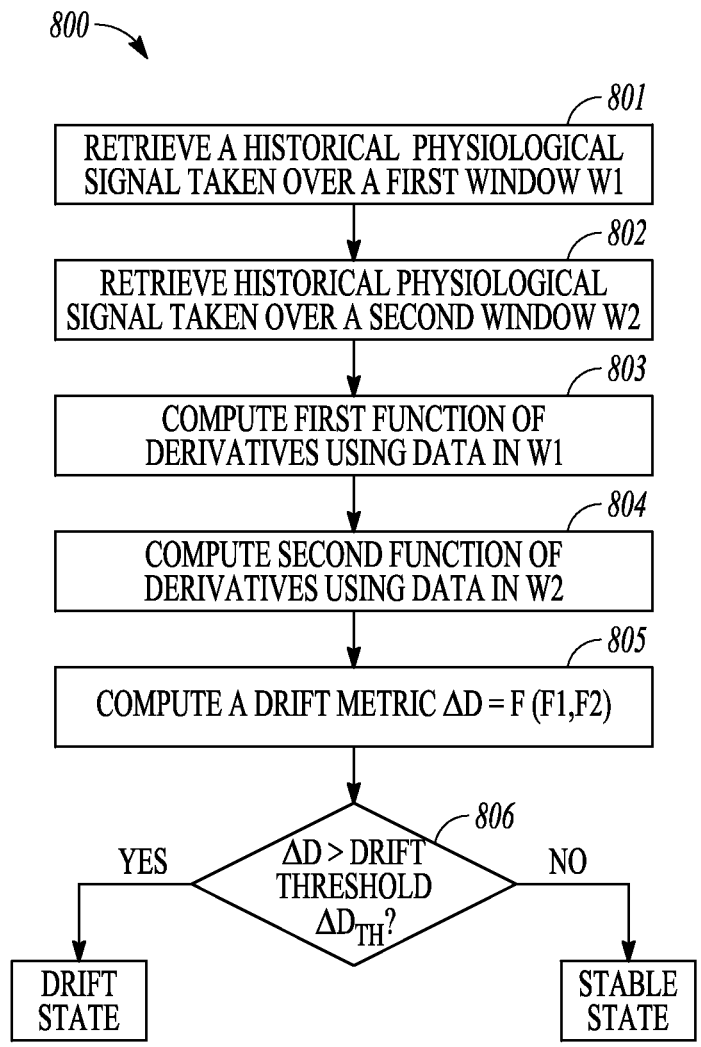
FIG. 8 illustrates an example of a method for determining a current physiologic state such as using a drift metric that can be computed as functions of one or more derivatives of a physiological signal.

FIG. 8 illustrates an example of a method 800 for determining present physiologic state such as using a calculated drift metric. Method 800 is an embodiment of 502. In an example, the method 800 can be performed by drift metric calculator circuit 330.

At 801, a first segment of physiological data is taken from the patient's historical physiological signal during a time window W1. At 802, a second segment of data is taken from the same physiological signal during a second time window W2. The beginning, end, or size of W2 may be programmed independently of the corresponding parameters of W1. In an example, the second time window W2 can be non-identical to the first time window W1. This can be achieved by programming at least one of the beginning, end, or size of W2 to a value different than that of W1. Then at 803, one or more of first or higher-order derivatives, or a combination of the derivatives thereof, denoted by F1, can be computed using the physiological data in W1. In an example, F1 can be the slope of a linear regression line fitting the data in W1. In another example, data in W1 can be fitted to a curve represented by a nonlinear function such as using a nonlinear regression analysis, and F1 can be the first or higher-order derivative of the fitted curve. Examples of the nonlinear function can include exponential function, logarithmic function, trigonometric function, power function, or Gaussian function. Similar process can be performed on the data in W2 at 804 to generate a second function F2. F1 and F2 can be computed using the same method. For example, if F1 is the slope of the linear regression line fitting data in W1, then F2 is the linear regression line fitting the data in W2.

At 805, a drift metric is computed as a function of F1 and F2. In an example, the drift metric can be the difference between F1 and F2. In another example, the drift metric can be the ratio between F1 and F2. The drift metric can then be compared to a drift threshold at 806. If the drift metric is greater than the drift threshold, then the physiologic state is deemed a drift state; otherwise, the physiologic state is deemed a stable state.

In some examples, more than one estimate of the drift metric can be calculated. Using more than one drift metric estimate is expected to increase the reliability of physiologic state determination. In an example, a plurality of data segments can be taken from the patient's historical physiological signal in N windows {W1, W2, ..., WN}, where N>2. These data windows can be selected such that they are either pair-wisely non-overlapping, or pair-wisely non-identical. Up to $N*(N-1)/2$ drift metric estimates may be computed using pair-wise windows as illustrated in FIG. 7 and FIG. 8. In another example, the data can be repetitively sampled from the two data segments of windows W1 and W2, and the drift metric can be computed after each data sampling. This process can end up with a plurality of drift metric estimates.

Figure 9:
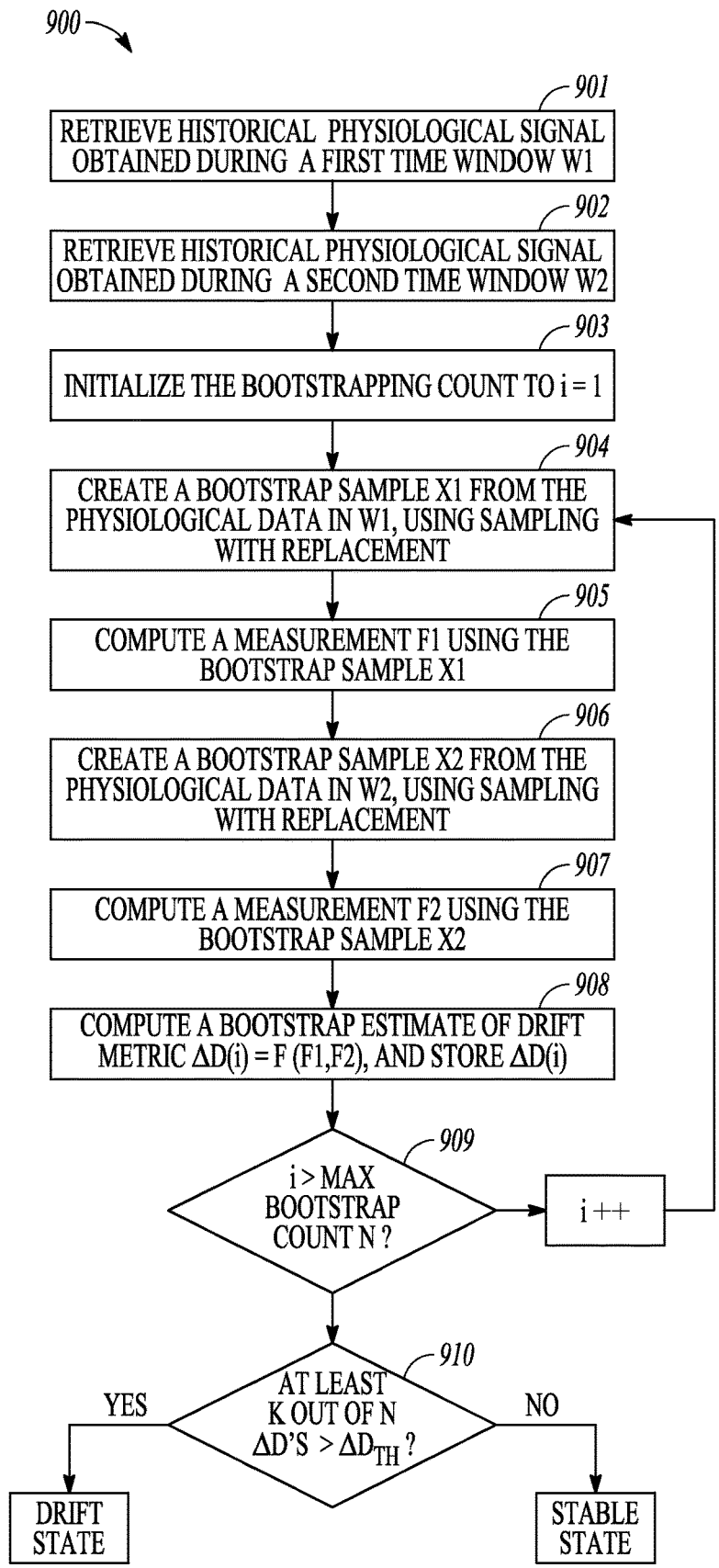
FIG. 9 illustrates an example of a method for determining a current physiologic state such as using a plurality of drift metric estimates.

FIG. 9 illustrates a specific example of a method 900 for determining the physiologic state such as using multiple drift metric estimates using bootstrapping. Bootstrapping technique can be especially usefully when the data is limited such that not enough data windows can be generated for multiple drift metric estimation. Method 900 is an embodiment of 502. In an example, the method 900 can be performed by drift metric calculator circuit 330.

At 901, a first segment of physiological data can be taken such as from the patient's historical physiological signal during a time window W1. At 902, a second segment of data can be taken such as from the same physiological signal during a second time window W2. The size of W2 (i.e., the number of data points in W2) can be the same as or different from the size of W1. At 903, the count of drift estimate is initialized to 1. A bootstrap sample X1 is created from the data segment in W1 at 904. X1 may have the same number of samples as the data segment from W1, and each sample in X1 can be taken from the segment in W1 with replacement. Therefore, X1 may contain duplicates of data samples taken from W1. Then, at 905, a measurement or function F1 can be computed from the bootstrap sample X1 such as using the same method as that at 703 or 803. Similar process can then be performed at 906 to obtain a bootstrap sample X2 from the physiological data in W2, and at 907 a measurement F2 such as the method at 704 or 804 can be computed from the bootstrap sample X2. A bootstrap estimate of drift metric $\Delta D(i)$ can be computed at 908, such as using the method at 705 or 805. This process of computing the bootstrap estimate of drift metric $\Delta D(i)$ from bootstrap samples X1 and X2 may be repeated until a predetermined number of bootstrapping operations (N) has been reached at 909. Then, the N drift metric estimates may be used to determine the physiologic state at 910. In some examples, each drift metric estimate can be compared to a specified threshold. If each of at least K out of N drift estimates is greater than a specified drift metric threshold $\Delta D_{TH}$, then the physiologic state is deemed drift state; otherwise the physiologic state is deemed stable state. The K-out-of-N criterion may be substituted by other criteria having equivalent effect, such as X % of the bootstrap estimates being greater than threshold $\Delta D_{TH}$, where X % takes the value between 0 and 100%. In an example, the drift metric $\Delta D$ can be the slope of a straight line connecting the centroids between the windows. By setting the drift metric threshold $\Delta D_{TH}$ to zero and the K-out-of-N criterion to 95%, the method 900 determines the present state to be drift state if more than 95% of the estimates of the slope of physiological signal are positive, a strong indication that the physiologic signal is drifting.

The physiologic state may also be determined such as using multiple drift metric estimates. In one embodiment of decision fusion, each drift metric can be compared to a threshold value to generate a decision of the physiologic state. The decisions from all the drift metric estimates can then be combined to yield a final decision of the physiologic state, such as using majority voting, weighted voting, or other liner or non-linear combinations of the decisions. In another example of the data fusion, the drift metric estimates computed from pair-wise data segments can be combined to form a composite drift metric, and the physiologic state can be determined such as using the composite drift metric. Methods of combining the drift metric estimates can include, for example, average, weighted average, or other linear or nonlinear operations.

Figure 10:
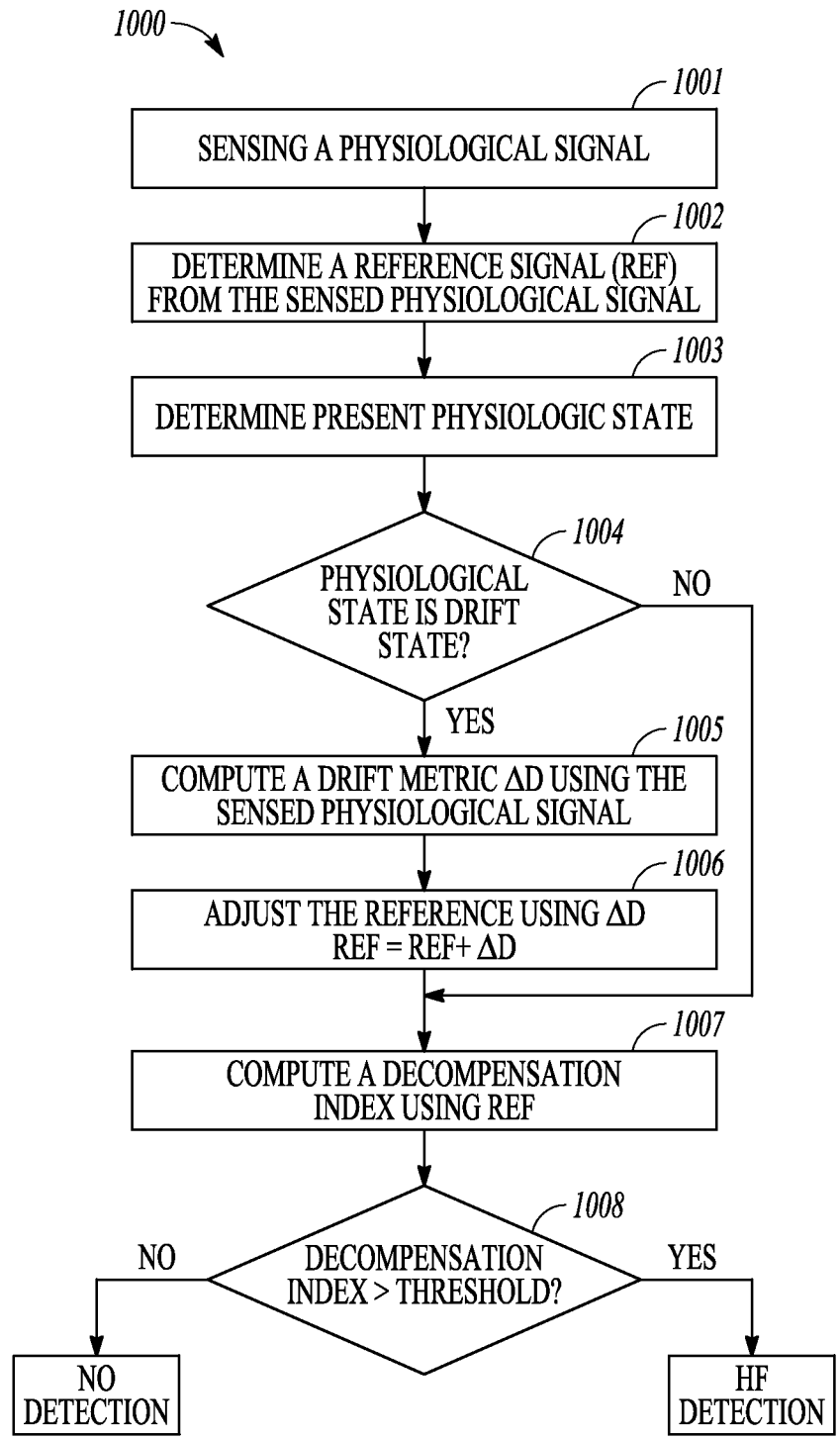
FIG. 10 illustrates an example of a method for detecting an event indicative of HF decompensation status such as using physiologic state information.

FIG. 10 illustrates an example of method 1000 for detecting an HF decompensation event from a physiological signal such as using the physiologic state information. The method 1000 is an embodiment of determining expected signal characteristics 503.

At 1001, a physiological signal is obtained. For example, physiological signal may be sensed from signal sensing circuit 202, a physiological sensor coupled to IMD 110, or data storage of patient's physiological signals residing in IMD 110 or external system 120. At 1002, a reference signal is computed from the sensed physiological signal. The reference signal may represent the trend of the signal intensity in history. The signal intensity can be represented by one or more of the signal amplitude or a function of the signal amplitude in the time domain, the signal's power spectral density, or a function of the power spectral density in the frequency domain. In an example, the reference signal can be a moving average of the physiological data over a specified time period. In another example, the reference signal can be low-pass or band-pass filtered physiological data with pre-determined filter coefficients.

The physiologic state can be determined at 1003 such as using one of the methods 600, 700, 800 or 900. If the present physiologic state is decided to be stable state at 1004, then the reference signal (Ref) is not updated. If the present physiologic state is deemed drift state, a drift metric ΔD can be computed at 1005. In an example, the drift metric ΔD can be computed such as using methods 705 or 805. In another example, if the sensed physiological signal for HF decompensation event detection is the same as the signal used for determining the present physiologic state, then the drift metric ΔD computed at 1003 can be retrieved and reused at 1005. The reference signal can then be updated at 1006 such as by adding the drift metric ΔD to the existing reference signal. The reference signal can be updated during drift state at 1006 if the drift metric ΔD meets a specified criterion. For example, the reference signal is updated if the absolute value of ΔD is greater than a pre-specified threshold.

At 1007, a decompensation index can be calculated using the sensed physiological signal and the reference signal. The decompensation index is a quantitative measure indicating the presence or severity of a physiologic condition precipitating an HF decompensation episode, such as excessive intrathoracic fluid accumulation. In an example, the decompensation index can be an accumulated deviation of the sensed physiological signal from the reference signal over time. The deviation may be computed as a difference between the intensity of the sensed physiological signal and the reference signal. In an example, the intensity of the sensed physiological signal can include a central tendency measure of the signal amplitude over a specified time (e.g., 3-10 days). In some embodiments, the decompensation index can be accumulated at 1007 if certain criterion is met, such as the difference between the signal intensity and the decompensation index being greater than a specified threshold. Other examples of decompensation index can include cumulative sum in detecting persistent shifts in the trended signal found in Brockway et al., U.S. Pat. No. 7,761,158, entitled "Detection of Heart Failure Decompensation Based on Cumulative Changes in Sensor Signals," filed Dec. 20, 2005, which is incorporated herein by reference in its entirety.

At 1008, the decompensation index can be compared to a specified threshold. If the decompensation index is greater than the threshold then an HF decompensation event is declared detected; otherwise, no HF decompensation event is detected.

The detection of an event indicative of HF decompensation can include calculation of at least one expected future signal characteristic. The expected future signals characteristics can be predicted such as using the historical data from the physiological signal. Examples of the signal characteristics can include signal intensity, signal trend, signal direction (i.e., consistent increase or consistent decrease in signal intensity), rate of change in signal intensity, or other statistical or morphological characteristics of the physiological signal. The future signal characteristics can be estimated such as using parametric or nonparametric signal modeling and prediction methods, such as linear predictive coding, autoregressive modeling, moving average and autoregressive modeling, neural networks, Markov model, or other nonlinear modeling methods. An HF decompensation event is deemed detected if at least one of the measured signal characteristics significantly deviates from the corresponding predicted signal characteristics.

Figure 11:
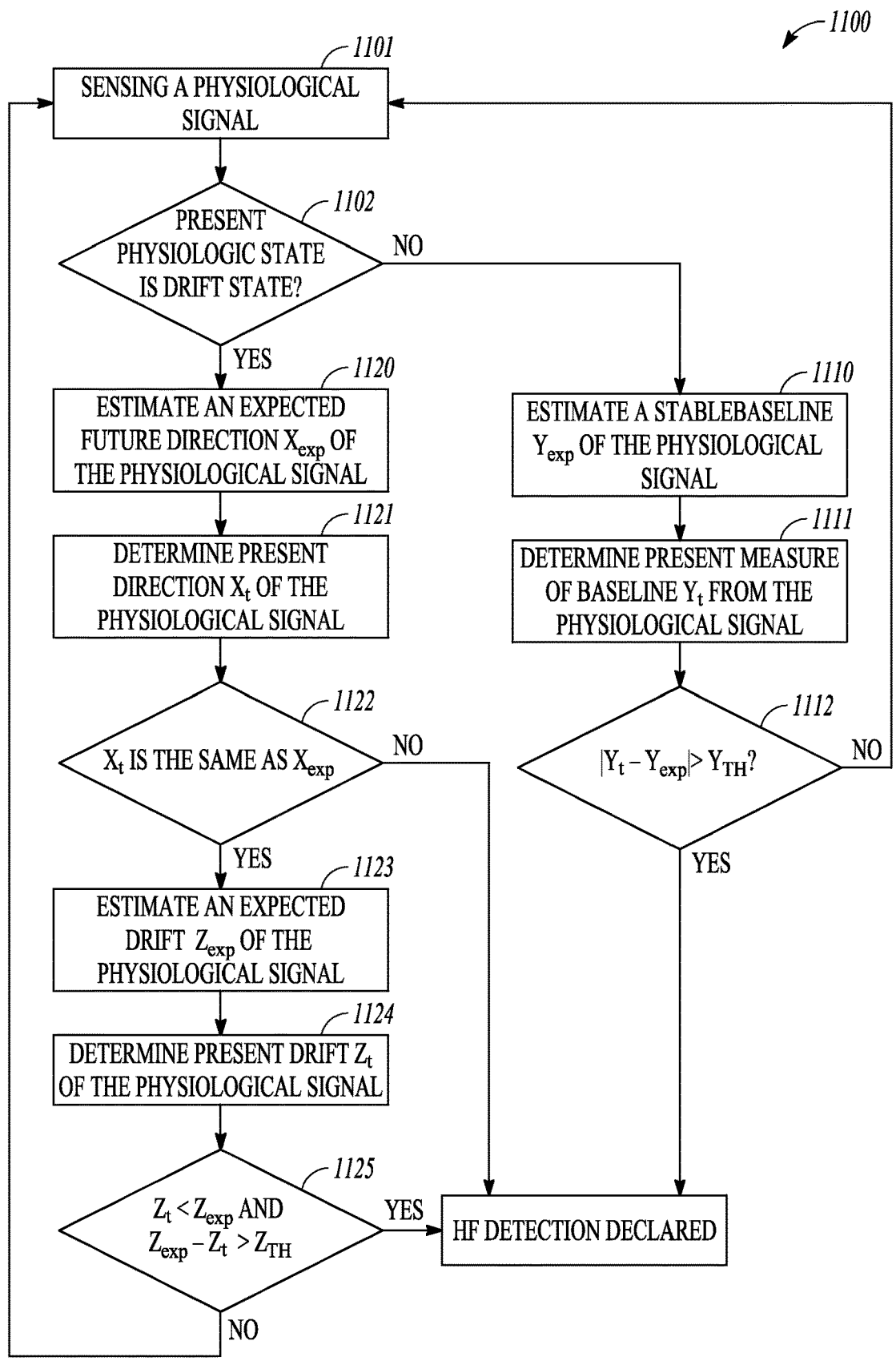
FIG. 11 illustrates an example of a method for detecting an event indicative of HF decompensation status such as using predicted signal characteristics.

FIG. 11 illustrates an example of method 1100 for detecting an HF decompensation event such as using expected future signal characteristics. The future signal characteristics can be selected and customized for the present physiologic state. In other words, depending on the present physiologic state, different expected future signal characteristics can be estimated to detect the HF decompensation event. The method 1100 is an embodiment of determining expected signal characteristics 503.

At 1101, a physiological signal can be obtained from either a physiologic sensor or a data source of patient's physiological signals. The physiologic state can be determined at 1102. In an example, this can be accomplished such as by using one of the methods 600, 700, 800, or 900.

Depending on the present physiologic state (as being either a drift state or stable state), different algorithms can be used to detect HF decompensation event. As illustrated in FIG. 11, if the present physiologic state is a drift state, then at 1120 an expected future direction of the physiological signal can be determined. The direction of the physiological signal indicates the trend of the physiological signal. Examples of the direction of the physiological signals can include: upward direction, which indicates that the signal intensity or the intensity of a metric computed from the signal consistently increases; downward direction, which indicates that the signal intensity or the intensity of a metric computed from the signal consistently decreases; or staying flat, which indicates that the signal intensity or the intensity of a metric computed from the signal remains at a stable level without consistent increase or decrease.

In an example, the expected future direction can be determined such as using the historical data. The expected direction can be determined by computing the first order derivative of the historical data. A positive derivative indicates an upward direction, and a negative derivative indicates a downward direction. The expected direction can also be determined from the difference between signal intensities at different time instants. For example, if the signal intensity at a later time instant is greater than the signal intensity at an earlier time instant, then an upward direction is indicated.

In another example, the expected future direction can be determined by empirical knowledge of the expected direction of the physiological signal under a known physiologic state. In an example of using intrathoracic impedance to detect an HF decompensation event, if the physiologic state is stable state, then the intrathoracic impedance is not expected to drift for reasons other than un-anticipated worsening of patient conditions such as worsening of HF status. Empirically, a downward direction of the intrathoracic impedance is anticipated because the worsening of HF is generally accompanied by excessive intrathoracic fluid buildup, causing a consistent decrease in impedance. In another example of using respiration rate signal to detect an HF decompensation event, an upward direction of respiration rate can be empirically determined at stable state because a buildup of intrathoracic fluid would generally cause an increase in respiration rate.

At 1121, present direction of the physiological signal is determined by, for example, comparing present physiological signal intensity to the signal intensity at an earlier time. The present direction and the expected future direction are compared at 1122 to determine whether the present direction is substantially different from the expected direction. An HF decompensation even is deemed detected if the present direction of the physiological signal is different than the expected future direction. For example, if the expected future direction is an upward direction (than is, the signal intensity or the intensity of a metric computed from the signal is expected to consistently increase), while the present direction of the signal is a downward direction (that is, the present signal intensity consistently decreases), then an HF decompensation detection is declared.

If the present direction is the same as the expected signal direction (e.g., both signal intensities are upward directions, that is, consistently increase), then an expected drift of the physiological signal can be determined at 1123. A drift is a quantitative measure of change or rate of change of the intensity of the physiological signal. In an example, the expected drift can be a slope of a linear regression line fitting a specified segment of historical physiological data. Then, a present drift of the physiological signal can be determined at 1124 from the physiological data. The present drift is then compared to the expected drift at 1125. If the present drift is less than the expected drift and the difference between the present drift and the expected drift is greater than a predetermined threshold, then an HF decompensation even is deemed detected. In an example of detecting HF decompensation using a transthoracic impedance signal, assume the expected drift can be +5 ohms/day and the present drift is +1 ohm/day, and the drift threshold is 2 ohms/day. Both the present direction and the expected direction are "upward direction" (i.e., signal intensity increases with time), as indicated by the positive drift value. However, the present drift is 4 ohms/day less than the expected drift. Because the difference is greater than the drift threshold, an HF detection is declared. If at 1125 the present drift is either greater than the expected drift, or the difference between the present drift and the expected drift is less than the predetermined threshold, then the drift phase sustains and the event causing the drift in physiological response (e.g., the post-implant pocket maturation) has not been resolved. Consequently, no HF decompensation detection is declared, and the detection process continues from 1101.

If at 1102 the present physiologic state is a stable state, then at 1110 a stable baseline of the physiological signal can be estimated. The stable baseline can be estimated such as using historical physiological data. In an example, the baseline can be a moving average of historical physiological signal. In other embodiments, the baseline is a low-pass or band-pass filtered historical physiological signal, including, for example, median filtered physiological signal or other central tendency measurement. A present measure of the baseline, computed from the physiological data at 1111, is then compared to the stable baseline at 1112. If the difference between the present baseline and the estimated stable baseline of the physiological signal is greater than a predetermined threshold, then an HF decompensation detection is declared. If this difference is less than or equal to the threshold, then no HF decompensation detection is declared, and the detection process continues from 1101.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An ambulatory medical device, comprising:
   a signal sensing circuit, configured to sense a physiologic signal indicative of the patient's heart failure (HF) decompensation status;
   a physiologic state analyzer circuit, including a drift metric calculator circuit, configured to calculate a drift metric using the sensed physiologic signal;
   wherein the physiologic state analyzer circuit is configured to determine a physiologic state of the patient using the calculated drift metric; and
   an HF decompensation event detector circuit, configured to detect an indication of HF decompensation status including applying a first algorithm to the sensed physiologic signal using a first expected future signal characteristic if the physiologic state indicates a drift state, and applying a different second algorithm to the sensed physiologic signal using a different second expected future signal characteristic if the physiologic state indicates a stable state;
   wherein the first algorithm includes a comparison of the sensed physiologic signal to the first expected future signal characteristic, and
   wherein the second algorithm includes a comparison of the sensed physiologic signal to the second expected future signal characteristic.

2. The device of claim 1, further comprising:
   a timer or a clock configured to determine a current elapsed time from a physiologic state trigger event; and
   a therapy circuit configured to initiate or modify a therapy based on the detected indication of HF decompensation status.

3. The device of claim 2, wherein the physiologic state analyzer is configured to:
   determine a time window ($T_{W1}$, $T_{W2}$) beginning at $T_{W1}$ and ending at $T_{W2}$, the values for $T_{W1}$ and $T_{W2}$ referenced to the physiologic state trigger event and determined using a type of the physiologic state trigger event or a configuration for sensing the physiologic signal; and
   determine the physiologic state using whether the elapsed time is within the time window ($T_{W1}$, $T_{W2}$).

4. The device of claim 3, wherein the physiologic state trigger event includes at least one of:
   a placement of the ambulatory medical device;
   a replacement of the ambulatory medical device;
   a surgical repositioning of the ambulatory medical device or its part;
   a delivery of therapy from the ambulatory medical device;
   a cardiac surgery;
   a discharge of the patient from a hospital; and
   a development of a medical condition indicative of a change of cardiopulmonary function.

5. The device of claim 1, wherein the drift metric calculator circuit is configured to calculate the drift metric using a comparison between (1) first measurements of the physiologic signal obtained during a first time window and (2) second measurements of the physiologic signal obtained during a non-overlapping second time window, and wherein the physiologic state analyzer is configured to determine the physiologic state using the calculated drift metric.

6. The device of claim 1, wherein the drift metric calculator circuit is configured to calculate the drift metric using a function of a first or higher order derivative of the physiological signal obtained from two or more non-identical time windows, and wherein the physiologic state analyzer is configured to determine the physiologic state using the calculated drift metric.

7. The device of claim 1, further comprising: an expected future signal characteristic calculator circuit configured to calculate the first and second expected future signal characteristics using the sensed physiologic signal according to the determined physiologic state, the first and second expected future signal characteristics each selected from an expected signal direction, an expected drift, and an expected baseline, and wherein the HF decompensation event detector circuit is configured to:
   if the physiologic state indicates the drift state, detect the indication of HF decompensation status using the first algorithm; or
   if the physiologic state indicates the stable state, detect the indication of HF decompensation status using the second algorithm; and
   an display unit configured to display the detected indication of HF decompensation status.

8. The device of claim 1, further comprising:
   an alarm unit configured to generate an alarm of the detected indication of HF decompensation status.

9. A method for operating an ambulatory medical device (AMD) associated with a patient to detect detecting an indication of heart failure (HF) decompensation status in the patient having an ambulatory medical device, the method comprising:
   sensing a physiologic signal indicative of the HF decompensation status;
   calculating a drift metric using the sensed physiologic signal;
   determining, via the AMD, a physiologic state of the patient using the calculated drift metric; and
   detecting, via the AMD, the indication of HF decompensation status including applying a first algorithm to the sensed physiologic signal using a first expected future signal characteristic if the physiologic state indicates a drift state, and applying a different second algorithm to the sensed physiologic signal using a different second expected future signal characteristic if the physiologic state indicates a stable state;

wherein the first algorithm includes a comparison of the sensed physiologic signal to the first expected future signal characteristic, and wherein the second algorithm includes a comparison of the sensed physiologic signal to the second expected future signal characteristic.

10. The method of claim 9, wherein the physiologic state is determined using the drift metric of the physiologic signal, the drift metric determined using at least one of:

a comparison between (1) first measurements of the physiologic signal obtained during a first time window and (2) second measurements of the physiologic signal obtained during a non-overlapping second time window; or a function of a first or higher order derivative of the physiological signal obtained from two or more non-identical time windows.

11. The method of claim 9, wherein the drift metric is determined using a comparison between (1) first measurements of the physiologic signal obtained during a first time window and (2) second measurements of the physiologic signal obtained during a non-overlapping second time window.

12. The method of claim 9, wherein the drift metric is determined using a function of a first or higher order derivative of the physiological signal obtained from two or more non-identical time windows.

13. The method of claim 9, wherein the physiologic state is determined using a plurality of estimates of the drift metric.

14. The method of claim 13, wherein the physiologic state is determined using a count of the estimates of the drift metric that satisfy at least one specified criterion.

15. The method of claim 9, further comprising determining the physiologic state using a current elapsed time since a physiologic state trigger event.

16. The method of claim 15, wherein the physiologic state trigger event includes at least one of:

a placement of the ambulatory medical device;
a replacement of the ambulatory medical device;
a surgical repositioning of the ambulatory medical device or its part;
a delivery of therapy from the ambulatory medical device;
a surgery;
a discharge of the patient from a hospital; and
a development of a medical condition indicative of a change of cardiopulmonary function.

17. The method of claim 15, wherein determining the physiologic state using the time from the physiologic state trigger event includes:

determining a programmable time window ($T_{W1}$, $T_{W2}$) beginning at $T_{W1}$ and ending at $T_{W2}$, including determining values for $T_{W1}$ and $T_{W2}$, referenced to the physiologic state trigger event, using (1) a type of the physiologic state trigger event or (2) a configuration for sensing the physiologic signal; and determining the physiologic state using whether the elapsed time is within the time window ($T_{W1}$, $T_{W2}$).

18. The method of claim 9, wherein detecting the indication of HF decompensation status comprises:

calculating the first and second expected future signal characteristics of the sensed physiologic signal using the determined physiologic state according to the determined physiologic state, the first and second expected future signal characteristics each selected from an expected signal direction, an expected drift, and an expected baseline; and if the physiologic state indicates the drift state, detecting the indication of HF decompensation status using the first algorithm; or if the physiologic state indicates the stable state, detecting the indication of HF decompensation status using the second algorithm.

19. An ambulatory medical device, comprising:

means for sensing a physiologic signal indicative of the HF decompensation status;

means for determining a physiologic state of the patient including means for determining a drift metric of the physiologic signal based on a comparison between (1) first measurements of the physiologic signal obtained during a first time window and (2) second measurements of the physiologic signal obtained during a non-overlapping second time window, or based on a function of a first or higher order derivative of the physiological signal obtained from two or more non-identical time windows; and means for detecting the indication of HF decompensation status including means for applying a first algorithm to the sensed physiologic signal using a first expected future signal characteristic if the physiologic state indicates a drift state, and means for applying a different second algorithm to the sensed physiologic signal using a different second expected future signal characteristic if the physiologic state indicates a stable state;

wherein the first algorithm includes a comparison of the sensed physiologic signal to the first expected future signal characteristic, and wherein the second algorithm includes a comparison of the sensed physiologic signal to the second expected future signal characteristic.

20. The device of claim 19, further comprising means for determining the first and second expected future signal characteristics using the sensed physiologic signal according to the determined physiologic state, the first and second expected future signal characteristics each selected from an expected signal direction, an expected drift, and an expected baseline, wherein the means for detecting the indication of HF decompensation status includes:

if the physiologic state indicates the drift state, means for detecting the indication of HF decompensation status using the first algorithm; or if the physiologic state indicates the stable state, means for detecting the indication of HF decompensation status using the second algorithm.

* * * * *